United States Patent
Ryu et al.

(10) Patent No.: US 10,261,064 B2
(45) Date of Patent: Apr. 16, 2019

(54) OPTICAL OIL COMPONENT SENSOR AND SENSING METHOD USING THE SAME

(71) Applicant: ELECTRONICS AND TELECOMMUNICATIONS RESEARCH INSTITUTE, Daejeon (KR)

(72) Inventors: Jin-Hwa Ryu, Daejeon (KR); Chan-Mo Kang, Daejeon (KR); Lee-Mi Do, Daejeon (KR); Kyu-Ha Baek, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 276 days.

(21) Appl. No.: 15/132,583

(22) Filed: Apr. 19, 2016

(65) Prior Publication Data

US 2017/0030883 A1 Feb. 2, 2017

(30) Foreign Application Priority Data

Jul. 31, 2015 (KR) .......................... 10-2015-0108835

(51) Int. Cl.
*G01N 21/41* (2006.01)
*G01N 33/22* (2006.01)
*G01N 33/28* (2006.01)

(52) U.S. Cl.
CPC .............. *G01N 33/22* (2013.01); *G01N 21/41* (2013.01); *G01N 33/28* (2013.01); *G01N 2201/08* (2013.01)

(58) Field of Classification Search
CPC ............. G01N 21/431; G01N 21/8507; G01N 2201/08; G01N 2201/082; G01N 33/28; G01N 33/21
See application file for complete search history.

(56) References Cited

U.S. PATENT DOCUMENTS 4,564,292 A * 1/1986 Omet .................. G01N 21/431
356/133
2012/0318074 A1 12/2012 Kyung et al.
(Continued)

FOREIGN PATENT DOCUMENTS

KR 20-0445853 Y1 9/2009

OTHER PUBLICATIONS

Jin Hwa Ryu et al., "Design and Analysis of Refractometer Based on Bend Waveguide Structure with Air Trench for Optical Sensor Applications," ETRI Journal, vol. 36, No. 5, Oct. 2014.

*Primary Examiner* — Thanh Luu
(74) *Attorney, Agent, or Firm* — LRK Patent Law Firm

(57) ABSTRACT

An optical oil component sensor and a sensing method using the sensor, which can identify similar fuel oil in real time. The optical oil component sensor includes a light source unit, a reference optical waveguide, configured to guide light thereinto, for receiving and outputting light emitted from the light source unit, a sensing optical waveguide, configured to guide light thereinto, for receiving and outputting light emitted from the light source unit, wherein a portion of the sensing optical waveguide is formed to be in contact with test target oil, a light-receiving unit for receiving both a reference light signal, output from the reference optical waveguide, and a test light signal, output from the sensing optical waveguide, and a control unit for identifying components of the test target oil by comparing optical properties of the reference light signal and the test light signal with each other.

17 Claims, 10 Drawing Sheets

(56) References Cited

U.S. PATENT DOCUMENTS

2015/0102802 A1    4/2015  Park et al.
2015/0136959 A1*   5/2015  Ryu .................. G01N 21/3577
                                                    250/227.11

* cited by examiner

OPTICAL OIL COMPONENT SENSOR AND SENSING METHOD USING THE SAME

CROSS REFERENCE TO RELATED APPLICATION

This application claims the benefit of Korean Patent Application No. 10-2015-0108835, filed Jul. 31, 2015, which is hereby incorporated by reference in its entirety into this application.

BACKGROUND OF THE INVENT/ON

1. Technical Field

The present invention relates generally to an optical oil component sensor and a sensing method using the sensor and, more particularly, to an optical oil component sensor and a sensing method using the sensor, which can identify similar fuel oil in real time by quantitatively measuring variation in refractive index.

2. Description of the Related Art

Similar fuel oil is produced by mixing an additive with refined fuel oil or by mixing similar materials so that a mixture has components similar to those of refined fuel oil. A lot of research into technology for distinguishing similar fuel oil from refined fuel oil has been conducted. Among this research, research using optical technologies has been highlighted from the standpoint of precision, discrimination time, etc.

FIG. 1 is a block diagram showing a conventional optical oil component test device.

In the conventional optical oil component test device shown in FIG. 1, a material to be analyzed is placed in a cell holder 2 between a light source 1 and a light signal detector tube 3. Further, the components of the material to be analyzed are tested by passing a light signal having a specific wavelength from the light source 1 through the material to be analyzed and analyzing the light signal, which has reached the detector tube 3. The light source used at this time must have the property of outputting a wavelength having the optical absorption characteristics of a representative material used to produce similar fuel oil. Further, the material to be analyzed must have the characteristic of being collected in the cell holder 2 and passing through the cell holder 2.

In relation to this, Korean Utility Model No. 0445853 discloses a fuel oil test device. More specifically, technology is disclosed for collecting fuel oil to be analyzed (similar gasoline or similar diesel oil), utilizing a light signal having a specific infrared wavelength as a light source, passing the light signal through the fuel oil, and measuring the absorption rate of the light signal, thus identifying similar fuel oil. The fuel oil test device is a sensor corresponding to the concept of a system composed of a light source, a cell holder, a detector tube, a calculation unit, and a display unit. The fuel oil test device measures oil components by using, for the light source, a light signal having the same wavelength as the intrinsic absorption wavelength of a specific component (toluene, thinner, lamp oil, or the like) added when similar fuel oil is produced, and by utilizing optical technology.

However, the conventional identification of similar fuel oil is limited in that it requires expensive equipment and takes a long time to analyze, and it is not easy to attempt to de/ermine the authenticity of oil. Technology developed to date has not yet fundamentally overcome the above problems.

The production and distribution of similar fuel oil are estimated to increase every year due to the characteristics of limited oil deposits, and production technology is also expected to be continuously developed. Therefore, there is urgently required the development of technology for identifying similar fuel oil.

SUMMARY OF THE INVENTION

Accordingly, the present invention has been made keeping in mind the above problems occurring in the prior art, and an object of the present invention is to provide an oil component sensor, which can be utilized in various chemical product fields including gasoline, lamp oil, and diesel oil, as well as similar fuel oil.

Another object of the present invention is to sense oil components in real time.

A farther object of the present invention is to provide an oil component sensor that can be implemented in a portable or fixed form.

In accordance with an aspect of the present invention to accomplish the above objects, there is provided an optical oil component sensor, including a light source unit; a reference optical waveguide, configured to guide light thereinto, for receiving and outputting light emitted from the light source unit a sensing optical waveguide, configured to guide light thereinto, for receiving and outputting the light emitted from the light source unit, wherein a portion of the sensing optical waveguide is formed to be in contact with test target oil; a light-receiving unit fir receiving both a reference light signal, output from the reference optical waveguide, and a test light signal, output from the sensing optical waveguide; and a control unit for identifying components of the test target oil by comparing optical properties of the reference light signal and the test light signal with each other.

The sensing optical waveguide may be configured such that the portion thereof is formed as a curved part, and the test target oil is in contact with the curved part.

The reference optical waveguide may be configured to include a curved part.

The curved part of the sensing optical waveguide and the curved part of the reference optical waveguide may be formed to have an identical radius of curvature.

An outer surface of the sensing optical waveguide except for the portion thereof may be covered with a clad, and a trench part may be formed around an outer surface of the portion of the sensing optical waveguide and is then capable of storing the test target oil therein.

An outer surface of the reference optical waveguide may be completely covered with a clad.

The optical oil component sensor may farther include an optical distributor formed in an input stage of the reference optical waveguide and the sensing optical waveguide and configured to receive the light emitted from the light source unit and distribute the light to the reference optical waveguide and to the sensing optical waveguide.

The sensing optical waveguide and the reference optical waveguide may be formed to have a structure of cores.

The optical oil component sensor may further include an additional sensing optical waveguide, configured to guide light thereinto, for receiving and outputting the light emitted from the light source unit, wherein a portion of the additional sensing optical waveguide is formed to be in contact with additional test target oil.

The light-receiving unit may be located beside the light source unit.

In accordance with an aspect of the present invention to accomplish the above objects, there is provided an optical oil component sensing method, including receiving, by a reference optical waveguide and a sensing optical waveguide, light emitted from a light source unit, wherein a portion of the sensing optical wave guide is in contact with test target oil; adding the light into the reference optical waveguide and the sensing optical waveguide; receiving, by a light-receiving unit, both a reference tight signal output from the reference optical waveguide and a test light signal output from the sensing optical waveguide; and identifying, by a control unit, components of the test target oil by comparing optical properties of the reference light signal and the test light signal with each other.

The optical oil component sensing method may further include receiving, by an optical distributor formed in an input stage of the reference optical waveguide and the sensing optical waveguide, the light emitted from the light source unit, and distributing the light to the reference optical waveguide and to the sensing optical waveguide.

The optical oil component sensing method may further include receiving, by an additional sensing optical waveguide, the light emitted from the light source unit, wherein a portion of the additional sensing optical waveguide is in contact with additional test target oil; guiding the light into the additional sensing optical waveguide; receiving, by the light-receiving unit, an additional test light signal output from the additional sensing optical waveguide; and identifying, by the control unit, components of the additional test target oil by comparing optical properties of the reference light signal and the additional test light signal with each other.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
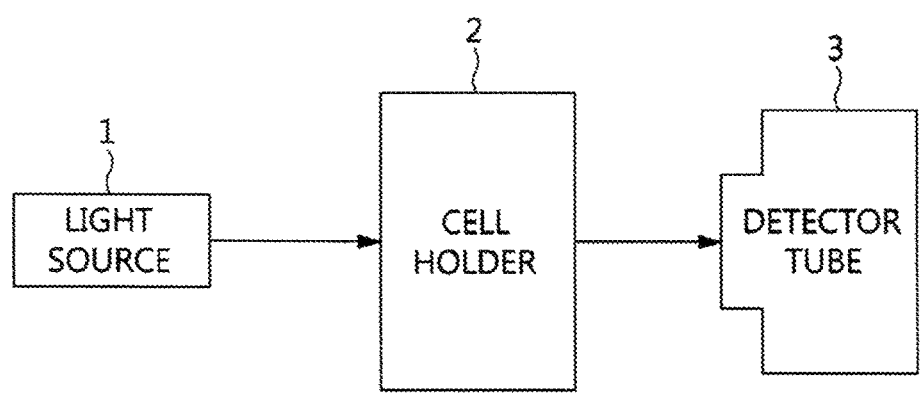
FIG. 1 is a block diagram illustrating a conventional optical oil component test device.

The present invention will be described in detail below with reference to the accompanying drawings. Repeated descriptions and descriptions of known functions and configurations which have been deemed to make the gist of the present invention unnecessarily obscure will be omitted below. The embodiments of the present invention are intended to fully describe the present invention to a person having ordinary knowledge in the art to which the present invention pertains. Accordingly, the shapes, sizes, etc. of components in the drawings may be exaggerated to make the description clearer.

Hereinafter, the structure and operation of an optical oil component sensor according to an embodiment of the present invention will be described in detail.

Figure 2:
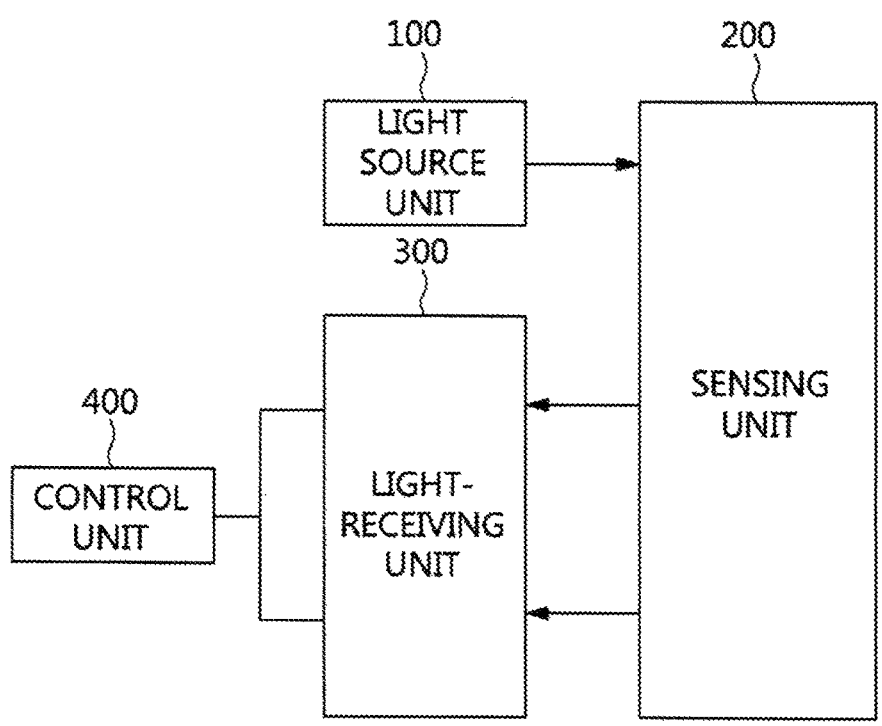
FIG. 2 is a block diagram showing an optical oil component sensor according to an embodiment of the present invention.
Figure 3:
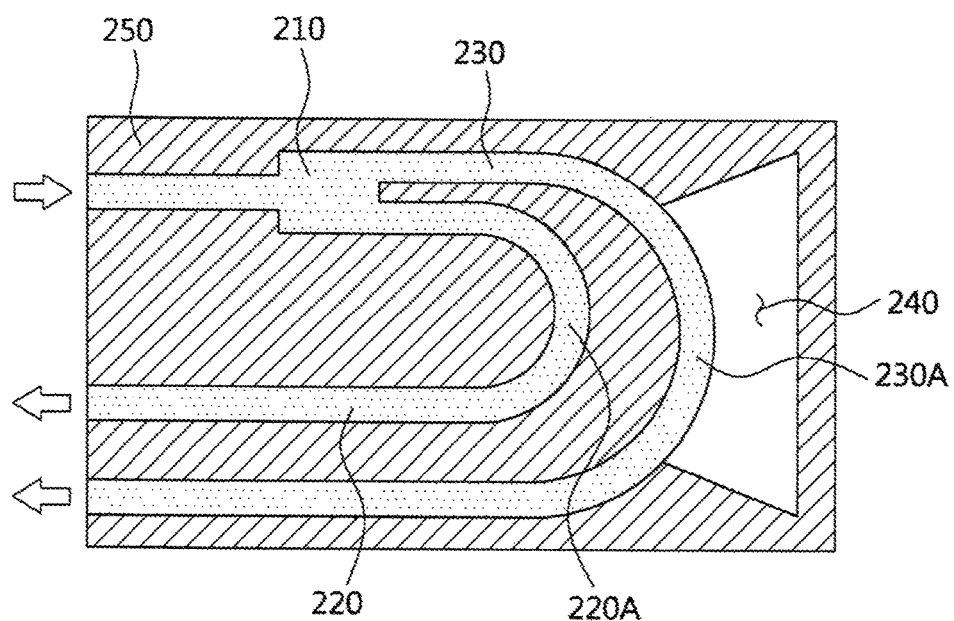
FIG. 3 is a conceptual diagram illustrating the sensing unit of the optical oil component sensor according to an embodiment of the present invention.
Figure 4:
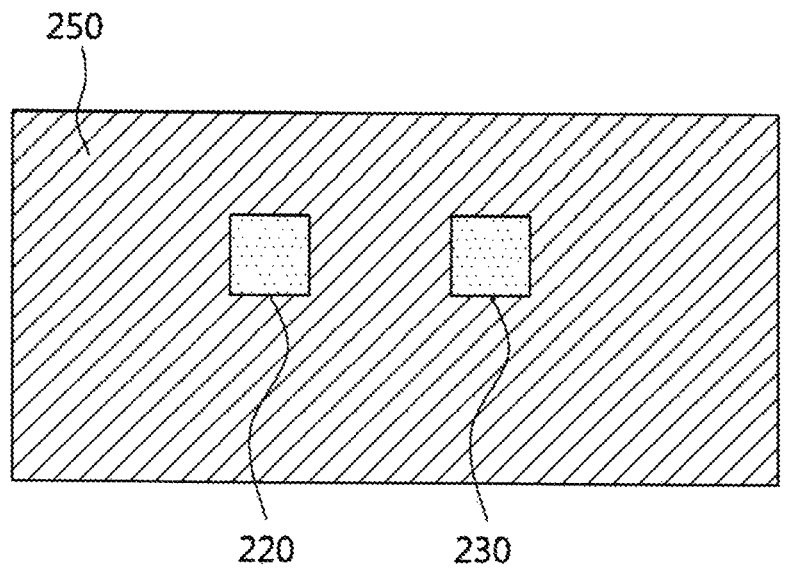
FIG. 4 is a sectional view illustrating the structures of a reference optical waveguide and a sensing optical waveguide in the sensing unit of FIG. 3.
Figure 5:
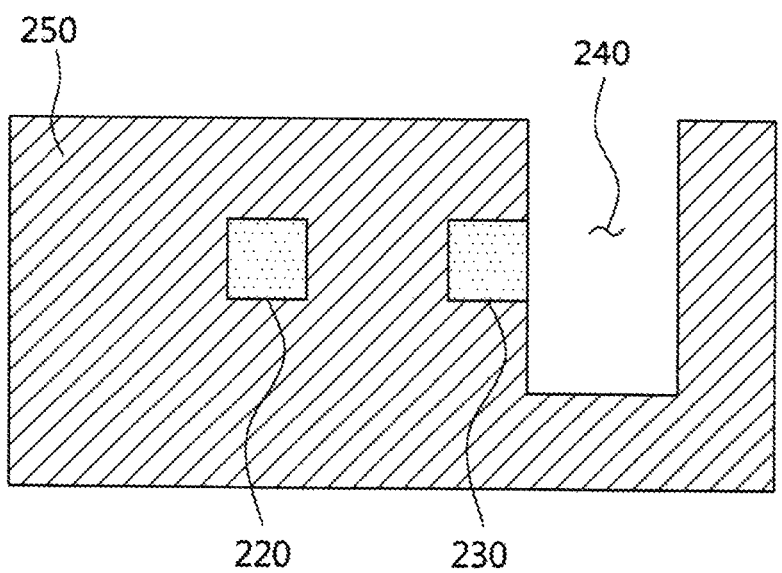
FIG. 5 is a sectional view illustrating the structures of curved parts of the reference optical waveguide and the sensing optical waveguide in the sensing unit of FIG. 3.

FIG. 2 is a block diagram showing an optical oil component sensor according to an embodiment of the present invention. FIG. 3 is a conceptual diagram illustrating the sensing unit of the optical oil component sensor according to an embodiment of the present invention. FIG. 4 is a sectional view illustrating the structures of a reference optical waveguide and a sensing optical waveguide in the sensing unit of FIG. 3. FIG. 5 is a sectional view illustrating the structures of curved parts of the reference optical waveguide and the sensing optical waveguide in the sensing unit of FIG. 3.

Referring to FIG. 2, an optical oil component sensor 10 according to an embodiment of the present invention includes a light source unit 100, a sensing unit 200, a light-receiving unit 300, and a control unit 400.

The light source unit 100 is configured to emit fight in a predetermined wavelength band.

Referring to FIGS. 3 to 5 together, the sensing unit 200 may include an optical distributor 210, a reference optical waveguide 220, a sensing optical waveguide 230, a trench part 240, and a clad 250.

The optical distributor 210 is formed in the input stage of the reference optical waveguide 220 and the sensing optical waveguide 230, which will be described later. Further, the optical distributor 210 receives light emitted from the light source unit 100, and distributes the light to the reference optical waveguide 220 and to the sensing optical waveguide 230.

The reference optical waveguide 220, which is configured to guide light thereinto, receives and outputs the light emitted from the light source unit 100. Further, the reference optical waveguide 220 may be formed to have the structure of a core. The reference optical waveguide 220 may be formed to include a curved part 220a. The outer surface of the reference optical waveguide 220 may be completely covered with the clad 250.

The sensing optical waveguide 230, which is configured to guide light thereinto, receives and outputs the light emitted from the light source unit. Further, the sensing optical waveguide 230 is configured such that a portion thereof is in contact with test target oil. Furthermore, the sensing optical waveguide 230 may be formed to have the structure of a core. A curved part 230a is formed in a portion of the sensing optical waveguide 230, and is in contact with the test target oil. Here, unlike the conceptual diagram of FIG. 2, the curved part 230a of the sensing optical waveguide 230 may be formed to have the same radius of curvature as the curved part 220a of the reference optical waveguide 220. By means of this, the refractive index and components of the test target oil may be checked by determining the difference between the properties of light signals output from the reference optical waveguide 220 and the sensing optical waveguide 230, which have the same radius of curvature. Also, the outer surface of the sensing optical waveguide 230, except for the portion of the sensing optical waveguide 230, may be covered with the clad 250.

In addition, the sensing optical waveguide may include multiple optical waveguides. That is, the sensing unit 200 may further include an additional sensing optical waveguide (not shown), which is configured to guide light thereinto and to receive and output light emitted from the light source unit 100, and which is formed such that a portion thereof is in contact with additional test target oil.

The trench part 240 may be formed around the portion of the sensing optical waveguide 230, that is, the curved pan 230a, and may store the test target oil therein. The curved part of the sensing optical waveguide 230 aligned with the trench part 240 has variation in refractive index due to external exposure. The trench part 240 functions to expose the core of the sensing optical waveguide 230 and store the test target oil with quantitative content. Therefore, a single light signal incident on the input stage branches into the reference optical waveguide 220 and the sensing optical waveguide 230. The light signal branching into the reference optical waveguide 220 exhibits uniform optical waveguiding properties, and the light signal branching into the sensing optical waveguide 230 exhibits optical waveguiding properties that are dependent on the material that is in contact with the structure of the trench part 240.

The clad 250 is formed to have a refractive index lower than those of the reference optical waveguide 220 and the sensing optical waveguide 230, that is, the cores. Therefore, the reference optical waveguide 220 and the sensing optical waveguide 230 are characterized in that, as the radius of curvature of a structure for guiding light is decreased, radiation loss is increased, resulting in a decrease in optical waveguiding properties. Further, optical waveguiding properties in the waveguides 220 and 230 are dependent on each other at the same radius of curvature due to the difference between the refractive indices of the cores and the clad 250. The present invention measures the components of the test target oil by utilizing the properties of the optical waveguides.

The light-receiving unit 300 receives both a reference light signal, output from the reference optical waveguide 220, and a test light signal, output from the sensing optical waveguide 230. In order for the light-receiving unit 300 to separately receive the light signal output from the reference optical waveguide 220 and the light signal output from the sensing optical waveguide 230, the receiving unit for receiving light signals may be divided into two parts. The light-receiving unit 300 may be formed in the same direction as the light source unit 100 with respect to the sensing unit 200. That is, the light-receiving unit 300 may be located beside the light source unit 100.

The control unit 400 identities the components of the test target oil by comparing the optical properties of the reference light signal and the test light signal with each other. Also, the control unit 400 may output the result of identification to the outside of the optical oil component sensor.

The optical oil component sensor 10 according to the embodiment of the present invention may be formed based on a planar optical circuit, and may then be utilized in both portable and fixed forms. The optical oil component sensor 10 may identify fuel oil in real time as the fuel oil is in contact with the sensing unit 200.

Figure 6A:
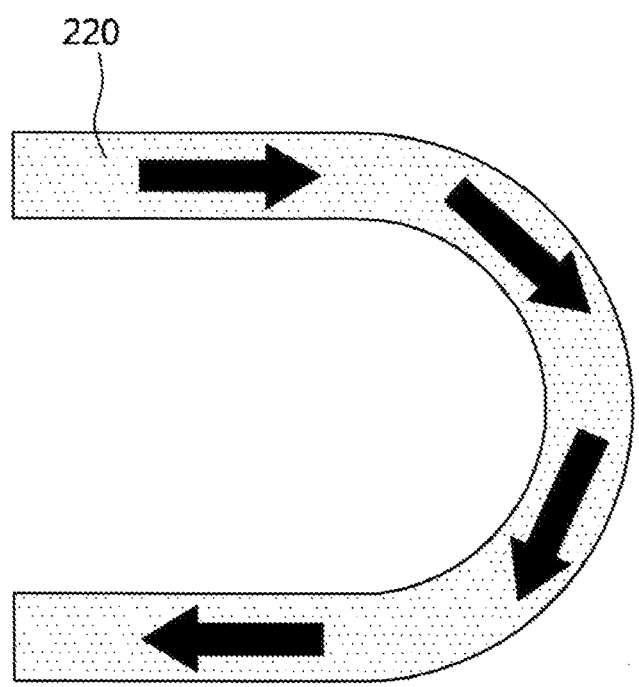
FIG. 6A is a diagram illustrating the waveguiding of light through the reference optical waveguide.

FIG. 6A is a diagram illustrating the waveguiding of light through the reference optical waveguide. FIGS. 6B to 6E are diagrams illustrating variation in the waveguiding of light through the sensing optical waveguide depending on variation in test target oil.

Figure 6B:
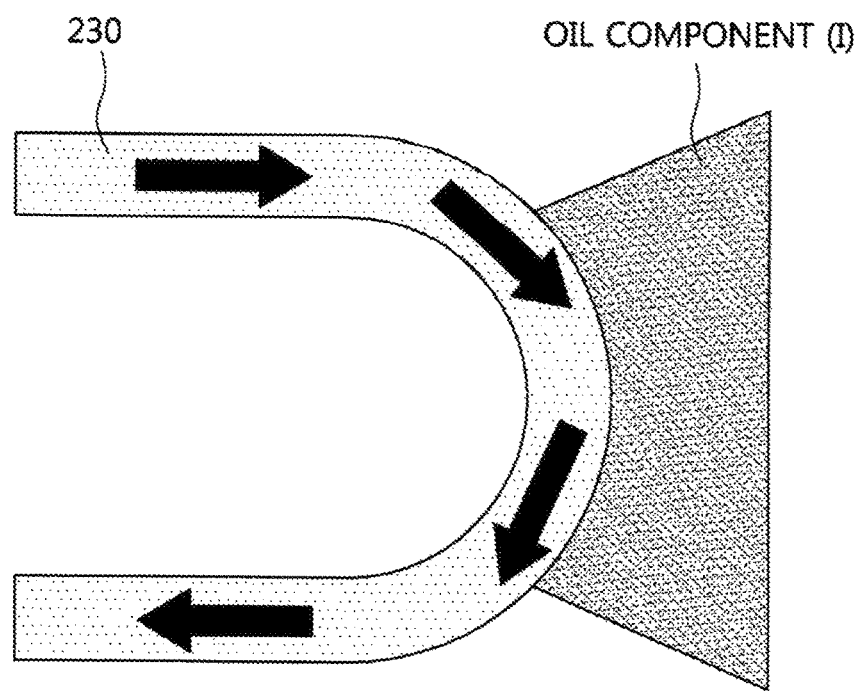
FIGS. 6B to 6E are diagrams illustrating variation in the waveguiding of light through the sensing optical waveguide depending on variation in test target oil.
Figure 6C:
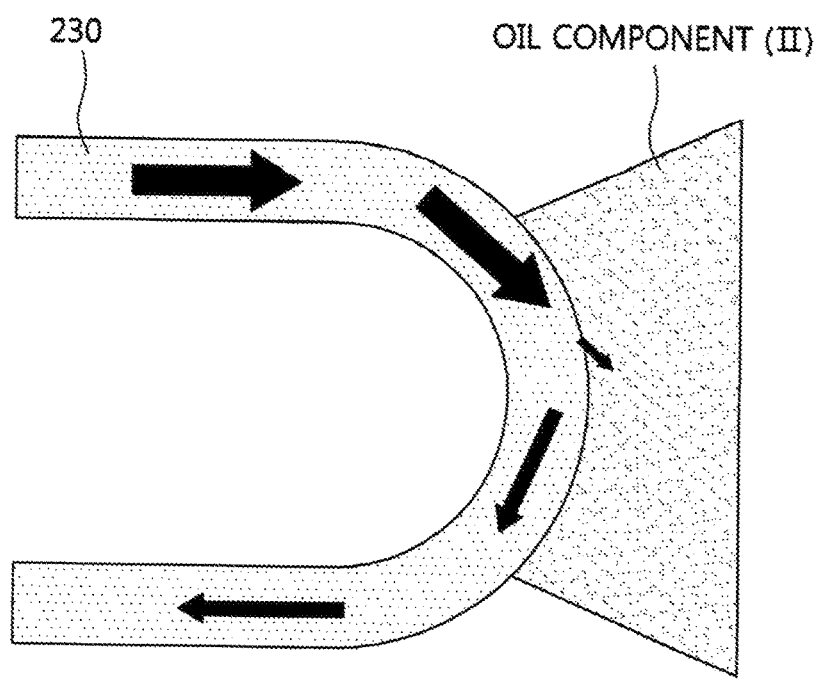
Figure 6D:
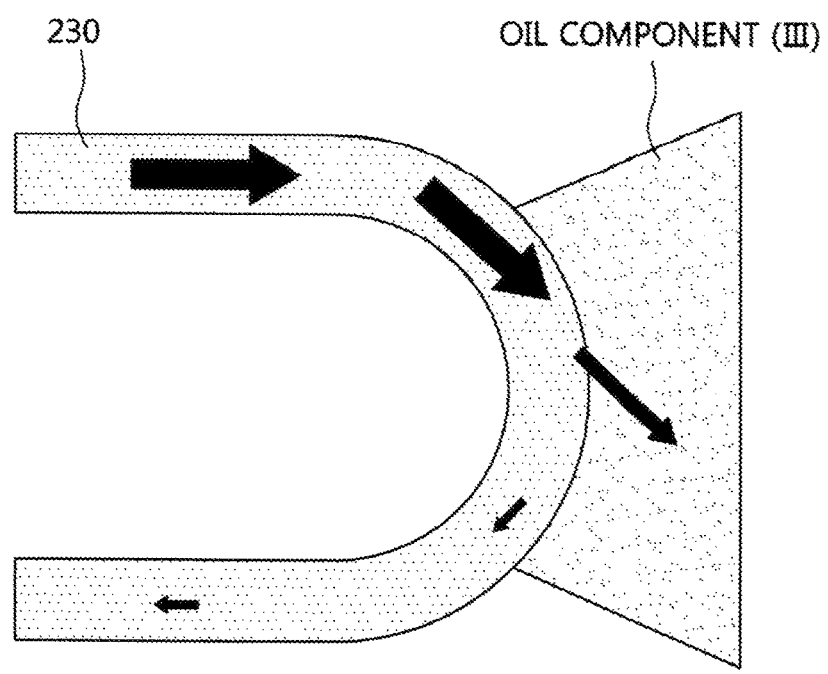
Figure 6E:
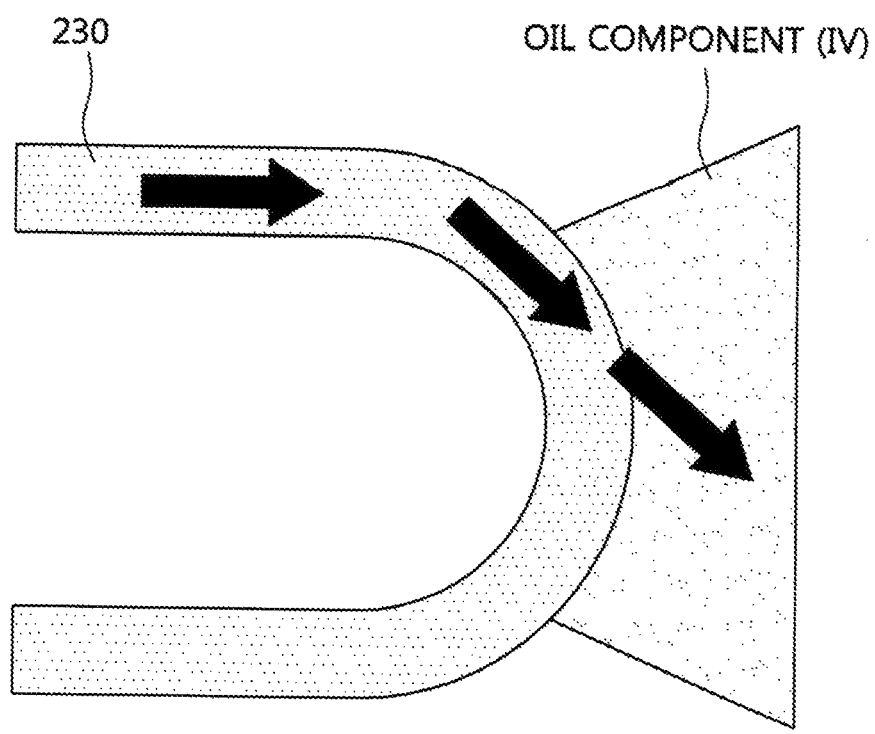

Referring to FIG. 6A, arrows indicate the waveguiding properties of the reference optical waveguide 220. The reference optical waveguide 220 has designed optical waveguiding properties regardless of oil components because the core for guiding the light signal is embedded in the clad. Further, FIGS. 6B to 6E illustrate the light signal waveguiding properties of the sensing optical waveguide 230 and show variation in the optical waveguiding properties depending on the oil component being in contact with the trench part. Such optical waveguiding properties are dependent on the type of contact material and the concentration of added material. The sensing optical waveguide 230, that is, the optical waveguide, in which the core, corresponding to a curved part, is exposed, may distinguish between gasoline, lamp oil, and diesel oil which have different refractive indices; and may also identify similar fuel oil having the properties of being dependent on the type and concentration of added material, based on variation in refractive index. FIG. 6B illustrates the optical, waveguiding properties of the sensing optical waveguide 230 depending on contact with an oil component having a low refractive index, and FIGS. 6C to 6E illustrate the optical waveguiding properties of the sensing optical waveguide 230 depending on contact with oil components, the refractive indices of which are sequentially increased in the sequence of FIGS. 6C, 6D, and 6E.

Hereinafter, an optical oil component sensing method according to an embodiment of the present invention will be described in detail.

Figure 7:
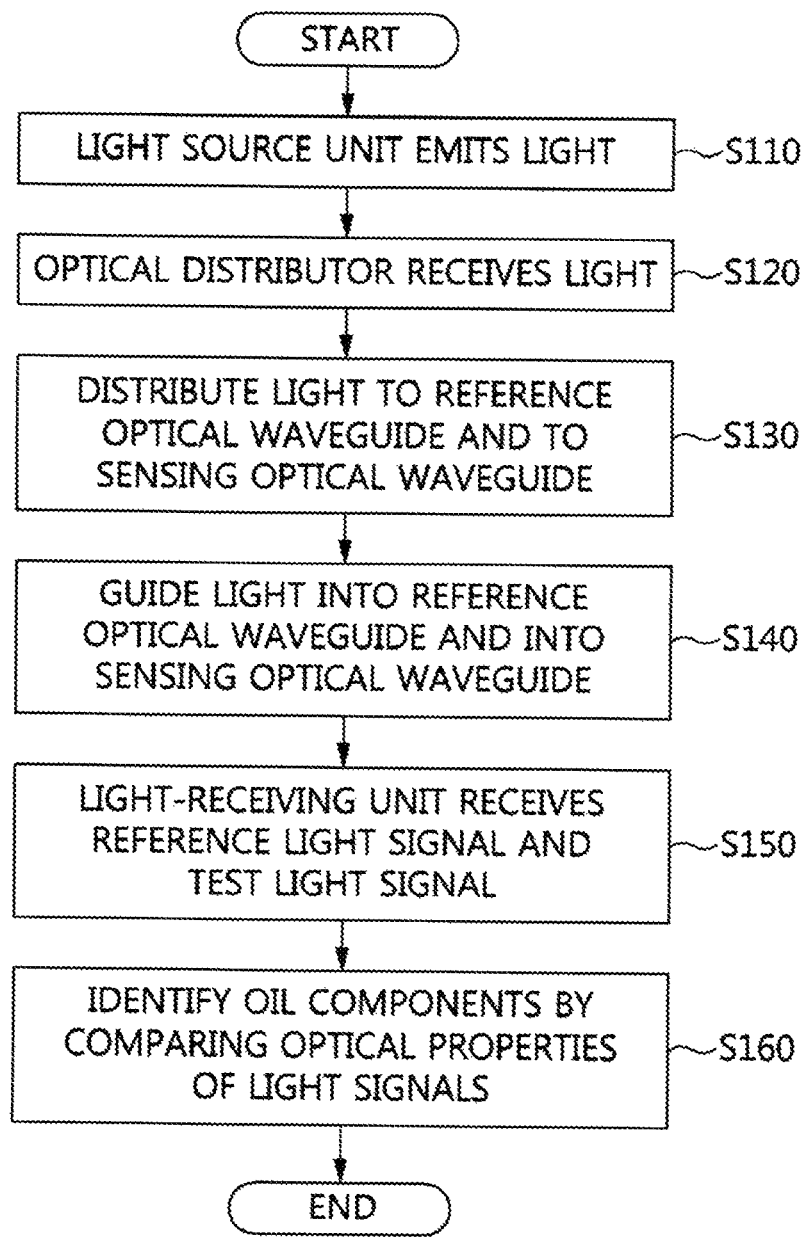
FIG. 7 is an operation flowchart illustrating an optical oil component sensing method according to an embodiment of the present invention.

FIG. 7 is an operation flowchart showing an optical oil component sensing method according to an embodiment of the present invention.

Referring to FIG. 7, in the optical oil component sensing method according to the embodiment of the present invention, when the light source unit emits light at step S110, the optical distributor receives the light at step S120.

Further, light distributed through the optical distributor is received by the reference optical waveguide and the sensing optical waveguide a portion of which is in contact with test target oil, at step S130. Here, the reference optical waveguide is formed to include a curved part. Also, a curved part is formed in a portion of the sensing optical waveguide, and the test target oil is in contact with the curved part. In this case, the curved part of the sensing optical waveguide and the curved part of the reference optical waveguide may have the same radius of curvature. The outer surface of the sensing optical waveguide, except for the portion thereof, is covered with a clad, and a trench structure (trench part) is formed around the outer surface of the portion of the sensing optical waveguide and is then capable of storing the test target oil therein. Also, the outer surface of the reference optical waveguide may be completely covered with a clad. In addition, the sensing optical waveguide and the reference optical waveguide may be formed to have the structure of cores.

Thereafter, the light received by the reference optical waveguide and the light received by the sensing optical waveguide are respectively guided into the reference optical waveguide and the sensing optical waveguide at step S140.

At step S150, the light-receiving unit receives both a reference light signal output from the reference optical waveguide and a test light signal output from the sensing optical waveguide at step S140. Here, the light-receiving unit may be located beside the light source unit.

Next, the control unit identifies the components of the test target oil by comparing the optical properties of the reference light signal and the test light signal with each other at step S160.

In addition, the optical oil component sensing method according to the embodiment of the present invention may further include the step of guiding light into an additional sensing optical waveguide, the step of the light-receiving unit receiving an additional test light signal output from the additional sensing optical waveguide, and the step of the control unit identifying the components of additional test target oil by comparing the optical properties of the reference light signal and the additional test light signal with each other.

In accordance with the present invention, variation in refractive index may be quantitatively measured, thus enabling similar fuel oil to be identified in real time. More specifically, the present invention may determine variation in refractive index characterized by being dependent on the components of a material, and may then be utilized in various chemical product fields including gasoline, lamp oil and diesel oil, as well as similar fuel oil.

Further, the present invention may be implemented in both portable and fixed forms because it is produced based on an optical circuit.

As described above, in the optical oil component sensor and optical oil component sensing method according to the present invention, the configurations and schemes in the above-described embodiments are not limitedly applied, and some or all of the above embodiments can be selectively combined and configured so that various modifications are possible.

What is claimed is:

1. An optical oil component sensor comprising:
   a light source unit;
   a single clad;
   a reference optical waveguide formed in and completely covered by the sing clad and configured to guide light thereinto, for receiving and outputting light emitted from the light source unit;
   a sensing optical waveguide formed in the single clad and configured to guide light thereinto for receiving and outputting the light emitted from the light source unit, wherein a sensing portion of the sensing optical waveguide is formed to be in contact with a test target oil;
   a light-receiving unit for receiving both a reference fight signal, output from the reference optical waveguide, and a test light signal, output from the sensing optical waveguide;
   a trench part formed in the single clad around an outer surface of the sensing portion of the sensing optical wave guide the trench part storing the test target oil therein; and
   a control unit for identifying components of the test target oil by comparing optical properties of the reference light signal and the test light signal with each other.

2. The optical oil component sensor of claim 1, wherein the sensing optical waveguide is configured such that the sensing portion thereof is formed as a curved part, and the test target oil is in contact with the curved part.

3. The optical oil component sensor of claim 2, wherein the reference optical waveguide is configured to include a curved part.

4. The optical oil component sensor of claim 1, further comprising an optical distributor formed in an input stage of the reference optical waveguide and the sensing optical waveguide and configured to receive the light emitted from the light source unit and distribute the light to the reference optical waveguide and to the sensing optical waveguide.

5. The optical oil component sensor of claim 1, wherein the sensing optical waveguide and the reference optical waveguide are formed to have a structure of cores.

6. The optical oil component sensor of claim 1, further comprising an additional sensing optical waveguide, configured to guide light thereinto, for receiving and outputting the light emitted from the light source unit, wherein a portion of the additional sensing optical waveguide is formed to be in contact with an additional test target oil.

7. The optical oil component sensor of claim 1, wherein the light-receiving unit is located beside the light source unit.

8. An optical oil component sensing method comprising:
   receiving, by a reference optical waveguide and a sensing optical waveguide, light emitted from a light source unit, wherein a sensing portion of the sensing optical wave guide is in contact with a test target oil;
   guiding the light into the reference optical waveguide and the sensing optical waveguide;
   receiving, by a light-receiving unit, both a reference light signal output from the reference optical waveguide and a test light signal output from the sensing optical waveguide; and
   identifying, by a control unit, components of the test target oil by comparing optical properties of the reference light signal and the test light signal with each other,
   wherein an outer surface of the reference optical waveguide is completely covered with a single clad,
   a trench part is formed in the single clad around an outer surface of the sensing portion of the sensing optical waveguide, the trench part storing the test target oil therein, and
   the reference optical waveguide the sensing optical waveguide and the trench part are formed in the single clad.

9. The optical oil component sensing method of claim 8, wherein the sensing optical waveguide is configured such that the sensing portion thereof is formed as a curved part, and the test target oil is in contact with the curved part.

10. The optical oil component sensing method of claim 9, wherein the reference optical waveguide is configured to include a curved part.

11. The optical oil component sensing method of claim 8, further comprising receiving, by an optical distributor formed in an input stage of the reference optical waveguide and the sensing optical waveguide, the light emitted from the light source unit, and distributing the light to the reference optical waveguide and to the sensing optical waveguide.

12. The optical oil component sensing method of claim 8, wherein the sensing optical waveguide and the reference optical waveguide are formed to have a structure of cores.

13. The optical oil component sensing method of claim 8, further comprising:
   receiving, by an additional sensing optical waveguide, the light emitted from the light source unit, wherein a portion of the additional sensing optical waveguide is in contact with an additional test target oil;
   guiding the light into the additional sensing optical waveguide;
   receiving, by the light-receiving unit, an additional test light signal output from the additional sensing optical waveguide; and
   identifying, by the control unit, components of the additional test target oil by comparing optical properties of the reference light signal and the additional test light signal with each other.

14. The optical oil component sensing method of claim 8, wherein the light-receiving unit is located beside the light source unit.

15. An optical oil component sensor comprising:
a light source unit;
a single clad;
a reference optical waveguide core formed in and completely covered by the single clad and configured to guide light thereinto, for receiving and outputting light emitted from the light source unit;
a sensing optical waveguide core formed in the single clad and configured to guide light thereinto for receiving and outputting the light emitted from the light source unit such that a sensing portion of the sensing optical waveguide core is continuous and includes an outer surface in contact with a test target oil;
a trench part formed in the single clad around the outer surface of the sensing portion of the sensing optical waveguide core, the trench part storing the test target oil therein;
a light-receiving unit for receiving both a reference light signal, output from the reference optical waveguide core, and a test light signal, output from the sensing optical waveguide core; and
a control unit for identifying components of the test target oil by comparing optical properties of the reference light signal and the test light signal with each other.

16. The optical oil component sensor of claim 15, wherein the sensing optical waveguide core is configured such that the sensing portion thereof is formed as a curved part, and the test target oil is in contact with the curved part.

17. The optical oil component sensor of claim 16, wherein the reference optical waveguide core is configured to include a curved part.

* * * * *